US009676755B2

(12) United States Patent
Fasel et al.

(10) Patent No.: US 9,676,755 B2
(45) Date of Patent: Jun. 13, 2017

(54) GRAPHENE NANORIBBONS WITH CONTROLLED MODIFICATIONS

(71) Applicants: BASF SE, Ludwigshafen (DE); EMPA—EIDGENOESSISCHE MATERIALPRUEFUNGS- UND FORSCHUNGSANSTALT, Duebendorf (CH); MAX-PLANCK-GESELLSCHAFT ZUR FOERDERUNG DER WISSENSCHAFTEN E.V., Munich (DE)

(72) Inventors: Roman Fasel, Zurich (CH); Pascal Ruffieux, Plasselb (CH); Klaus Muellen, Cologne (DE); Jinming Cai, Zurich (CH); Xinliang Feng, Mainz (DE); Reinhard Berger, Mainz (DE)

(73) Assignees: BASF SE, Ludwigshafen (DE); EMPA-EIDGENOESSISCHE MATERIALPRUEFUNGS-UND FORSCHUNGSANSTALT, Duebendorf (CH); MAX-PLANCK-GESELLSCHAFT ZUR FOERDERUNG DER WISSENSCHAFEN E.V., Munich (DE)

( * ) Notice: Subject to any disclaimer, the term of this patent is extended or adjusted under 35 U.S.C. 154(b) by 0 days.

(21) Appl. No.: 14/402,560

(22) PCT Filed: May 13, 2013

(86) PCT No.: PCT/IB2013/053886
§ 371 (c)(1),
(2) Date: Nov. 20, 2014

(87) PCT Pub. No.: WO2013/175342
PCT Pub. Date: Nov. 28, 2013

(65) Prior Publication Data
US 2015/0158850 A1    Jun. 11, 2015

Related U.S. Application Data

(60) Provisional application No. 61/651,008, filed on May 24, 2012.

(30) Foreign Application Priority Data

May 24, 2012  (EP) .................................... 12169326

(51) Int. Cl.
| C07D 403/10 | (2006.01) |
| C01B 31/04 | (2006.01) |
| C07D 215/18 | (2006.01) |
| C07D 237/26 | (2006.01) |
| C07D 239/72 | (2006.01) |
| C07D 209/56 | (2006.01) |
| B82Y 30/00 | (2011.01) |
| B82Y 40/00 | (2011.01) |

(52) U.S. Cl.
CPC ............ *C07D 403/10* (2013.01); *B82Y 30/00* (2013.01); *B82Y 40/00* (2013.01); *C01B 31/0438* (2013.01); *C01B 31/0446* (2013.01); *C07D 209/56* (2013.01); *C07D 215/18* (2013.01); *C07D 237/26* (2013.01); *C07D 239/72* (2013.01); *C01B 2204/06* (2013.01); *C01B 2204/065* (2013.01)

(58) Field of Classification Search
CPC . C01B 31/04; C01B 31/0407; C01B 31/0415; C01B 2204/00; C01B 2204/02; C01B 2204/04; C01B 2204/06; C01B 2204/065; C01B 2204/20; C01B 2204/22; C01B 2204/24; C01B 2204/28; C01B 2204/30; C01B 2204/32
USPC ......................................... 423/448
See application file for complete search history.

(56) References Cited

U.S. PATENT DOCUMENTS

| 7,968,872 B2 | 6/2011 | Schaefer et al. |
| 2010/0028681 A1 | 2/2010 | Dai et al. |
| 2010/0047154 A1 | 2/2010 | Lee et al. |
| 2011/0097258 A1 | 4/2011 | Lee et al. |
| 2012/0021250 A1 | 1/2012 | Lee et al. |
| 2012/0068161 A1* | 3/2012 | Lee ........................ B82Y 30/00 257/29 |

FOREIGN PATENT DOCUMENTS

| CN | 101913599 | 12/2010 |
| WO | 2011/018144 | 2/2011 |
| WO | 2013/072292 A1 | 5/2013 |

OTHER PUBLICATIONS

Haskins, et al., Control of Thermal and Electronic Transport in Defect-Engineered Graphene Nanoribbons, ACS NANO 2011; 5(5): 3779-3787.*
International Search Report Issued Oct. 3, 2013 in PCT/IB13/053886 filed May 13, 2013.
Written Opinion of the International Searching Authority issued Oct. 3, 2013 in PCT/IB13/053886 filed May 13, 2013.
(Continued)

*Primary Examiner* — Daniel C McCracken
(74) *Attorney, Agent, or Firm* — Oblon, McClelland, Maier & Neustadt, L.L.P.

(57) ABSTRACT

The present invention relates to a graphene nanoribbon, comprising a repeating unit which comprises at least one modification, wherein the modification is selected from a heteroatomic substitution, a vacancy, a $sp^3$ hybridization, a Stone-Wales defect, an inverse Stone-Wales defect, a hexagonal $sp^2$ hybridized carbon network ring size modification, and any combination thereof.

12 Claims, 8 Drawing Sheets

(56) References Cited

OTHER PUBLICATIONS

Cai, J. et al., "Atomically precise bottom-up fabrication of graphene nanoribbons", Nature, vol. 466, pp. 470-473, 2010.
Zeng, H. et al., "Effect of N doping and Stone-Wales defects on the electronic properties of graphene nanoribbons",The European Physical Journal B, vol. 79, pp. 335-340, 2011.
Zhang, Hang, et al., "Aryl Functionalization as a Route to Band Gap Engineering in Single Layer Graphene Devices", ACS Publications, Nano Letters, vol. 11, 2011, pp. 4047-4051.
Girão, Eduardo Costa, et al., "Emergence of Atypical Properties in Assembled Graphene Nanoribbons", Phys. Rev. Lett., vol. 107, 2011, pp. 1-5.
Usachov, D., et al., "Nitrogen-Doped Graphene: Efficient Growth, Structure, and Electronic Properties", ACS Publications, Nano Letters, vol. 11, 2011, pp. 5401-5407.
Wu, Jishan, et al.. "From Branched Polyphenylenes to Graphite Ribbons", Macromolecules, vol. 36, 2003, pp. 7082-7089.
Tomar, Manisha, et al., "Facile Synthesis and Coupling of Functionalized Isomeric Biquinolines", Tetrahedron Letters, vol. 53, 2012, pp. 285-288.
Wakabayashi, Katsunori, et al., "Electronic States of Graphene Nanoribbons and Analytical Solutions", Science Technology Advanced Materials, vol. 11, 2010, pp. 1-18.
Batzill, Matthias, "The Surface Science of Graphene: Metal Interfaces, CVD Synthesis, Nanoribbons, Chemical Modifications, and Defects", Surface Science Reports, vol. 67, 2012, pp. 83-115.
Liu, Hongtao, et al., "Chemical Doping of Graphene", Journal of Materials Chemistry, vol. 21, 2011, pp. 3253-3496.
Wang, Xinran, et al., "N-Doping of Graphene Through Electrothermal Reactions with Ammonia", Science Magazine, vol. 324, 2009, pp. 768-771.
Fogel, Yulia, et al., "Graphite Nanoribbons with Dibenzo[e,l]pyrene Repeat Units: Synthesis and Self-Assembly", Macromolecules Article, vol. 42, 2009, 6878-6884.
Holt, P.F., et al., "Polycyclic Cinnoline Derivatives. Part XV. Nitration of Benzo[f]naphtho[2,1-c]cinnohne and the Synthesis of Symmetrical Dibromo-derivatives", Journal of Chemical Society.
Extended European Search Report issued Dec. 4, 2012 in Patent Application No. 12169326.1.
Xiaoyin Yang, et al., "Two-Dimensional Graphene Nanoribbons" Journal of the American Chemical Society, vol. 130, No. 13, XP55025794, 2008, pp. 4216-4217.
Lukas Dössel, et al., "Graphene Nanoribbons by Chemists: Nanometer-Sized, Soluble, and Defect-Free" Angewandte Chemie International Edition, vol. 50, XP55022100, 2011, pp. 2540-2543.
Daniel J. Gregg, et al., "Structurally Characterized Hetero-Oligopolyphenylenes: Synthetic Advances Toward Next-Generation Hetercsuperbenzenes" Chemistry—a European Journal, vol. 12, XP002687357, 2006, pp. 3043-3052.
Daniel J. Gregg, et el., "Extending the Nitrogen-Heterosuperbenzene Family: The Spectroscopic, Redox, and Photophysical Properties of "Half-Cyclized" N-1/2 HSB and Its Ru(II) Complex" Inorganic Chemistry, vol. 44, No. 16, XP002687358, 2005, pp. 5654-5660.
Zhiyong Wang, et al., "The electronic properties of graphene nanoribbons with boron/nitrogen codoping" Applied Physics Letters, vol. 96, XP012131615, 2010, pp. 243110-1-243110-3.
J. N. B. Rodrigues, et al., "Zigzag graphene nanoribbon edge reconstruction with Stone-Wales defects" Physical Review B, vol. 84, XP002686045, 2011, pp. 155435-1-155435-15.
European Search Report issued Feb. 5, 2016 in Patent Application No. 13794615.8.

\* cited by examiner

A

F

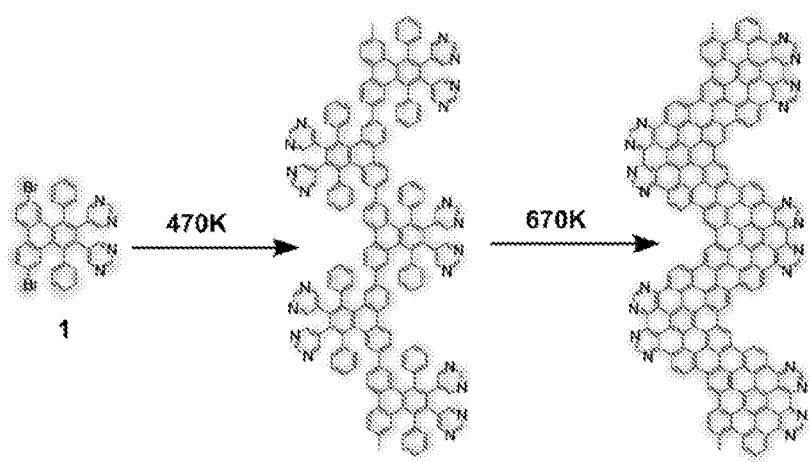
Figure 14
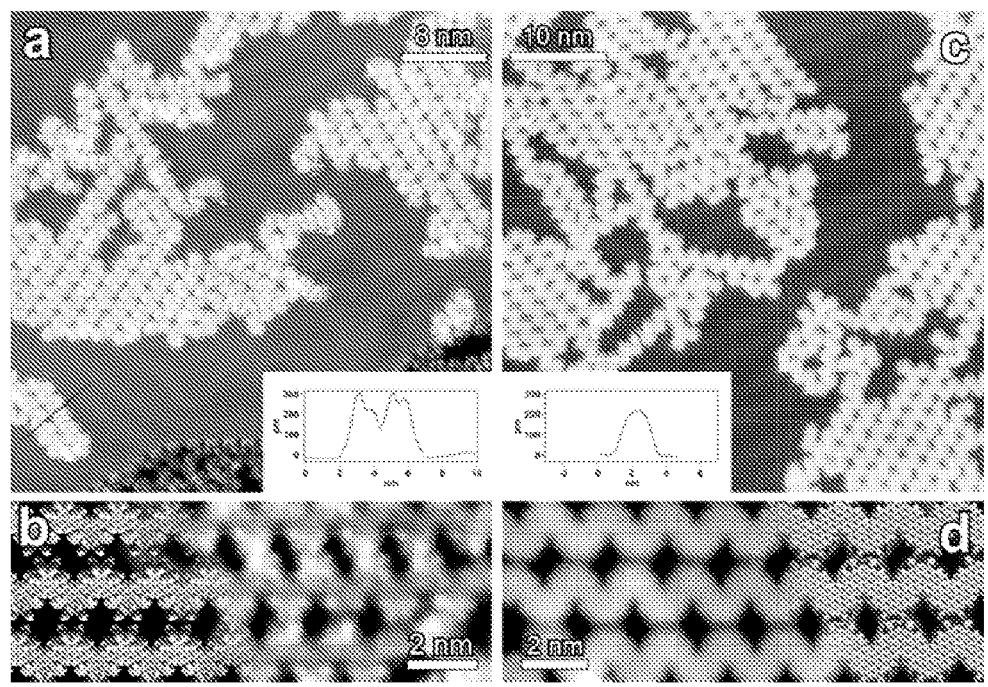
Figures 15a-d

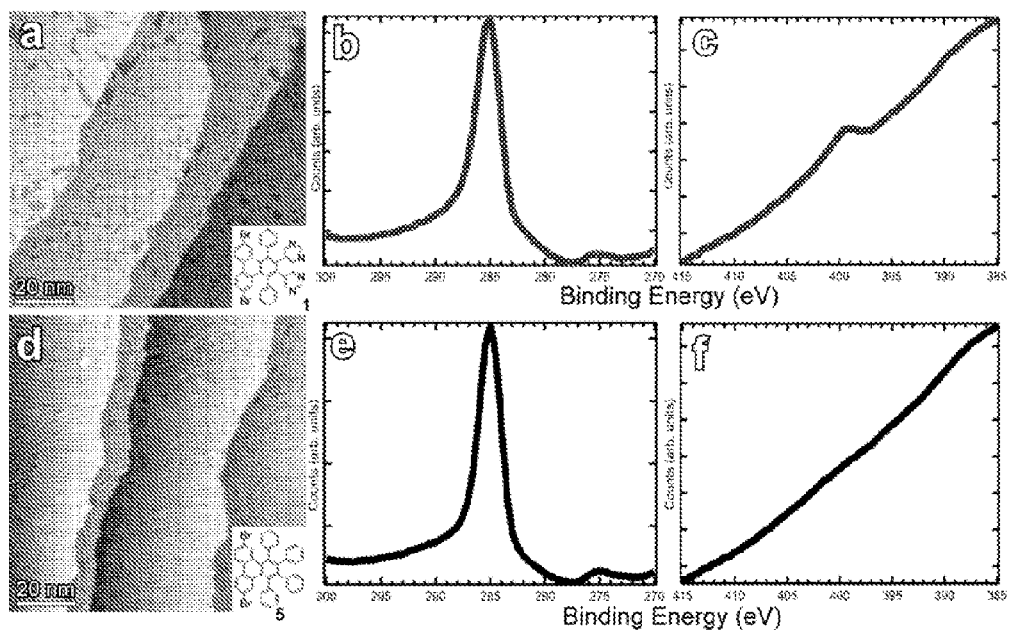
Figures 16a-f

GRAPHENE NANORIBBONS WITH CONTROLLED MODIFICATIONS

The present invention relates to graphene nanoribbons with controlled modifications and a method for preparing such graphene nanoribbons.

Graphene, an atomically thin layer from graphite, has received considerable interest in physics, material science and chemistry since the recent discovery of its appealing electronic properties. These involve superior charge carrier mobility and the quantum Hall effect. Moreover, its chemical robustness and material strength make graphene an ideal candidate for applications ranging from transparent conductive electrodes to devices for charge and energy storage.

An important challenge for the use of graphene, a semi-metallic material (zero-gap semiconductor), in semiconductor devices is its lack of a controllable band-gap. A band-gap can be opened in graphene by introducing controlled modifications, for instance by substituting carbon atoms within the graphene plane with heteroatoms (also called substitutional doping) such as nitrogen and boron as described e.g. by H. Liu et al. (J. Mater. Chem., 2011, 21, 3335-3345) or D. Usachov et al. (Nano Lett. 2011, 11, 5401-5407), resulting in a p- or n-doped semiconducting character of graphene. Substitutional heteroatom functionalization of graphene is preferably taking place at defect sites and grain boundaries. Control of the extent of substitution and spatial distribution of substitution sites is not feasible using this approach.

Graphene nanoribbons (GNRs) are linear structures that are derived from the parent graphene lattice. Their characteristic feature is high shape-anisotropy due to the increased ratio of length over width. The structural basis of GNRs is a hexagonal $sp^2$ hybridized carbon network which is terminated at the edges either by hydrogen atoms or any other organic or inorganic substituent. Currently, their usage in yet smaller, flatter and faster carbon-based devices and integrated circuits is being widely discussed in material science. In contrast to graphene, armchair-type GNRs exhibit an electronic band gap that is strongly dependent on their width. At the same time the edge structure of the GNRs has a strong impact on the electronic properties. Computational simulations and experimental results on smaller nanographenes suggest that GNRs exhibiting nonbonding π-electron states at zigzag edges can be used as active component in spintronic devices.

Graphene nanoribbons (GNRs) are promising building blocks for novel graphene based electronic devices. Beyond the most important distinction between electrically conducting zig-zag edge (ZGNR) and predominantly semiconducting armchair edge ribbons (AGNR), more general variations of the geometry of a GNR allow for gap tuning through one-dimensional (1D) quantum confinement. In general, increasing the ribbon width leads to an overall decrease of the band gap, with superimposed oscillation features that are maximized for armchair GNRs (AGNRs).

The introduction of controlled modifications into the hexagonal $sp^2$ hybridized carbon network of GNRs has the potential to further increase the versatility of these building blocks for use in electronic devices. Substitutional heteroatom functionalization of a carbon atom in the GNR hexagonal $sp^2$ hybridized carbon network is one possible approach for introduction of modifications. By selection of appropriate heteroatoms and substitution sites, GNR of identical dimensions can for instance be made into p- or n-type semiconductors.

Beside the substitution of carbon atoms in the GNR hexagonal $sp^2$ hybridized carbon network by heteroatoms, a very limited number of alternative carbon network modification types in GNRs are known. For instance vacancies, Stone-Wales defects, inverse Stone-Wales defects and other defects are described in M. Batzill, Surface Science Reports 2012, 67, 83-115. The reaction of the $sp^2$ hybridized GNR carbon atom with radicals such as carbon, fluorine, or hydrogen radicals may introduce $sp^3$ hybridization modifications into the hexagonal $sp^2$ hybridized carbon network as described e.g. in H. Zhang et al., Nano Letters 2011, 11, 4047-4051.

Standard top-down fabrication techniques for the fabrication of GNR such as cutting graphene sheets e.g. using lithography, unzipping of carbon nanotubes (e.g. described in US2010/0047154 and US2011/0097258), or using nanowires as a template are not suitable for ribbons narrower than 5-10 nm, because the edge configuration is not precisely controlled and they do not yield ribbons of monodisperse width. For high-efficiency electronic devices, the ribbons need to be less than 10 nm wide, their width needs to be precisely controlled and, importantly, their edges need to be smooth because even minute deviations from the ideal edge shapes seriously degrade the electronic properties.

Recently, substitutional N-functionalization of GNRs has been demonstrated by H. Dai et al. (Science, 2009, 324, 768). Nitrogen substitution was achieved using electrothermal reaction with ammonia on prefabricated (by top-down techniques) GNRs. The resulting N-substituted GNRs were found to be predominantly nitrogen substituted at the edges and behaving as n-doped semiconductor, but control over the exact location and the extent of substitution is not feasible when using this approach, and therefore well controlled n-doping is not possible.

The strong interest in p- and n-doped graphene nanoribbons derives from the fact that p- and n-type semiconductors are the fundamental building blocks of modern high-speed- and opto-electronics. In this respect, doped GNRs might provide a completely new concept for the realization of (opto-)electronic devices. Indeed, using GNRs as building blocks rather than semiconducting crystalline thin films, the unique quantum properties of the constituents can be fully exploited. Band gap tuning between different components of a heterojunction can then simply be achieved by varying the modification type, e.g. the heteroatom substituent (dopant), in analogy to the at present most commonly employed silicon semiconductor technology. Due to the inherent limitations of lithographic methods and of other known approaches to fabricate graphene nanostructures, however, the experimental realization of GNRs with controlled modifications in the hexagonal $sp^2$ carbon network with the required high precision has remained elusive. Bottom-up approaches based on cyclodehydrogenation reactions in solution (e.g. Dössel, L.; Gherghel, L.; Feng, X.; Müllen, K. Angew. Chem. Int. Ed. 50, 2540-2543 (2011)) or on solid substrates (e.g. Cai, J.; et al. Nature 466, 470-473 (2010)) have recently emerged as promising routes to the synthesis of nanoribbons and nanographenes with precisely controlled structures.

At least two general types of precisely controlled linear nanoribbon structures can be distinguished. In a first type, the edges are forming a straight line along the nanoribbon, while in another type, sometimes called 'chevron' type or 'nanowiggles' (described e.g. in Phys. Rev. Lett. 2011 (107), 135501), the edges are lying on a corrugated or saw-toothed line. The latter case can also be described as a periodic repetition of nonaligned graphitic nanoribbon domains seamlessly stitched together without structural defects.

The edges of the graphene nanoribbons may be terminated either with hydrogen atoms and/or with any other organic or inorganic groups.

For solution-based approaches using oligo phenylene precursors a polymer is typically prepared in a first step which is subsequently converted into the graphitic structure by Scholl-type oxidative cyclodehydrogenation. However, the design of the parent monomer must be carefully adjusted in order to guarantee for a suitable arrangement of the aromatic units upon the chemistry-assisted graphitization into the final GNR structure. J. Wu, L. Gherghel, D. Watson, J. Li, Z. Wang, C. D. Simpson, U. Kolb, and K. Müllen, Macromolecules 2003, 36, 7082-7089 report the synthesis of graphitic nanoribbons obtained by intramolecular oxidative cyclodehydrogenation of soluble branched poly-phenylenes, which were prepared by repetitive Diels-Alder cycloaddition of 1,4-bis(2,4,5-triphenylcyclopentadienone-3-yl)benzene and diethynylterphenyl. The obtained graphene ribbons are not linear but rather contain statistically distributed "kinks" due to the structural design of the polyphenylene precursor.

Y. Fogel, L. Zhi, A. Rouhanipour, D. Andrienko, H. J. Räder, and K. Müllen, Macromolecules 2009, 42, 6878-6884 report the synthesis of a homologous series of five monodisperse ribbon-type polyphenylenes, with rigid dibenzopyrene cores in the repeat units, by microwave-assisted Diels-Alder reaction. The size of the obtained polyphenylene ribbons ranges from 132 to 372 carbon atoms in the aromatic backbone which incorporates up to six dibenzopyrene units. Because of the flexibility of the back-bone and the peripheral substitution with dodecyl chains, the polyphenylene ribbons are soluble in organic solvents. In a further reaction step, ribbon-type polycyclic aromatic hydrocarbons (PAHs) are prepared by cyclodehydrogenation.

All these solution based methods have so far only led to graphene nanoribbons that do not contain controlled modifications of the hexagonal $sp^2$ carbon network, such as e.g. substitution of carbon atoms in the hexagonal carbon network by heteroatoms or vacancies.

A surface-confined bottom-up approach to controlled graphene nanoribbons has been described in J. Cai et al., Nature 466, pp. 470-473 (2010). However, no graphene nanoribbons that do contain controlled modifications of the hexagonal $sp^2$ hybridized carbon networks, such as e.g. substitution of carbon atoms in the hexagonal carbon network by heteroatoms or vacancies have been obtained.

It is an object of the present invention to provide a graphene nanoribbon (GNR) containing modifications (i.e. deviations from the ideal hexagonal $sp^2$ hybridized carbon network structure), wherein the position of modifications and the distance between modifications as well as the number and nature of modifications is precisely controlled. A further object of this invention is a process for preparing such a graphene nanoribbon.

According to a first aspect of the present invention, the object is solved by providing a graphene nanoribbon, comprising a repeating unit RU1 which comprises at least one modification, wherein the modification is selected from a heteroatomic substitution, a vacancy, a $sp^3$ hybridization, a Stone-Wales defect, an inverse Stone-Wales defect, a ring size modification in the hexagonal $sp^2$ hybridized carbon network, and any combination thereof.

In the graphene nanoribbon of the present invention, the position of modifications and the distance between modifications as well as the number of modifications per repeating unit is precisely controlled. If the modification site is for example a heteroatomic substitution modification site, a substitutionally heteroatom functionalized graphene nanoribbon (GNR) is provided wherein the position of heteroatom substituents and the distance between substituents as well as the number of heteroatom substituents per repeating unit is precisely controlled.

Similar to conventional polymers, the graphene nanoribbon of the present invention has its specific repeating unit. The term "repeating unit" relates to the part of the nanoribbon whose repetition would produce either the complete ribbon (except for the ends) or, if the GNR is made of two or more segments, one of these segments (except for the ends). The term "repeating unit" presupposes that there is at least one repetition of said unit. In other words, if the repeating unit is referred to as RU1, the GNR or one of its segments is made of n RU1 units with n≥2 (i.e. (RU1)$_n$ with n≥2). The upper limit depends on the desired final properties of the graphene nanoribbon and/or the process conditions, and can be e.g. n≤2500.

The graphene nanoribbon may comprise just one repeating unit RU1 (with n repetitions as indicated above). However, it is also possible that the graphene nanoribbon of the present invention comprises two or more different repeating units RU1, RU2, . . . RUm, thereby resulting in a segmented graphene nanoribbon.

The graphene nanoribbon can be non-segmented. Alternatively, the graphene nanoribbon can be a segmented graphene nanoribbon which comprises at least two different graphene segments S1 and S2 covalently linked to each other, wherein the neighbouring segments S1 and S2 have different repeating units RU1 and RU2.

As indicated above, the modification is selected from a heteroatomic substitution, a vacancy, a $sp^3$ hybridization, a Stone-Wales defect, an inverse Stone-Wales defect, a ring size modification in the hexagonal $sp^2$ hybridized carbon network, and any combination thereof.

A heteroatomic substitution modification (in the following also referred to as substitutional functionalization) means the replacement of at least one carbon atom in the hexagonal $sp^2$ hybridized carbon network with at least one heteroatom or heteroatomic group. The substitution may be anywhere within the graphene hexagonal $sp^2$ hybridized carbon network.

Modification by heteroatomic substitution is exemplified graphically on a section of an armchair graphene nanoribbon in FIG. 1, e.g. at the edges ($X_1$), peripheral ($X_2$), or central ($X_3$). FIG. 1 is just for exemplifying heteroatomic substitution modifications but does not show a repeating unit. A graphene nanoribbon comprising a repeating unit which comprises heteroatomic substitution modifications is shown in FIG. 2. The figure shows a central and a peripheral nitrogen substitution modification where one carbon atom is replaced by one nitrogen atom and a substitution modification at the edges where two neighboring carbon atoms have been replaced by two nitrogen atoms. Double bonds and hydrogen atoms have been omitted for sake of clarity.

A heteroatomic substitution modification (substitutional functionalization) also includes the case where two or even three neighbouring carbon atoms are replaced by one heteroatom and cases where one or more than one neighbouring carbon atoms are replaced by more than one heteroatom. A selection of examples for this case is shown in FIG. 3 in a section of a zig-zag graphene nanoribbon (replacement of 2 carbons by one heteroatom=$X_4$, replacement of 3 carbons by one heteroatom=$X_5$, replacement of more then one carbon by more than one heteroatom=$X_6$). FIG. 3 is just for exemplifying these kinds of heteroatomic substitution modification but does not show a repeating unit. As shown in FIG.

3, the regular hexagonal sp² hybridized carbon network structure of the graphene ribbon can be disturbed and form irregular sections with 5-, 6-, 7-, and 8-membered cyclic structures.

FIG. 4 shows heteroatom substitution modifications in a chevron type armchair GNR: The figure shows central heteroatom substitution modifications where six neighboring carbon atoms have been replaced by three nitrogen and three boron atoms and substitution modifications at the edge where one carbon atom has been replaced by a phosphor atom. Double bonds and hydrogen atoms have been omitted for sake of clarity The heteroatom substitution may also be accompanied by the formation of vacancies in the hexagonal sp² hybridized carbon network because for instance the valency of the heteroatom may be different from the valency of carbon or because more than one carbon atom has been replaced by the heteroatom. A selection of examples of heteroatom substitutions accompanied by vacancies is shown in FIGS. 5 and 6. FIGS. 5 and 6 are just for exemplifying these kinds of heteroatomic substitution modification in combination with vacancy modifications but do not show a repeating unit. As shown in the Figures, the heteroatom substitution may also result in concomitant substitution of at least one additional carbon atom in the hexagonal sp² hybridized carbon network by a hydrogen atom or halogen, especially fluorine. A valency of the heteroatom differing from the valency of carbon may also result in formation of charged heteroatom positions, where the charge can be positive or negative, as shown in FIG. 5.

A vacancy modification means the elimination of one to sixteen neighboring carbon atoms in the hexagonal sp² hybridized carbon network. Due to a vacancy modification, there is at least one atom less if compared to an ideal hexagonal sp² hybridized carbon network. This is exemplified by the structure shown in FIG. 7, containing a single vacancy (elimination of one carbon atom) and a double vacancy (elimination of two neighboring carbon atoms) site. FIG. 7 is just for exemplifying these kinds of modifications by vacancies but does not show a repeating unit. In the case of a vacancy modification elimination of a carbon atom may also result in concomitant substitution of at least one additional carbon atom in the hexagonal sp² hybridized carbon network by a hydrogen atom or halogen, especially fluorine.

FIG. 8 shows a GNR comprising a repeating unit with vacancy modifications. The figure shows a vacancy modification at the edge where one carbon atom is missing and a central vacancy modification with six missing carbon atoms (a complete missing hexagon). Double bonds and hydrogen atoms have been omitted for sake of clarity.

A sp³ hybridization modification means the addition of at least one substituent to a sp² hybridized carbon atom in the hexagonal sp² hybridized carbon network, resulting in a sp³ hybridized carbon atom. The substituent R may for instance be hydrogen, a halogen (e.g. fluorine), or a carbon substituent. This kind of modification is exemplified by the structure of FIG. 9 showing a single sp³ hybridization modification and two modifications with two neighboring sp³ hybridization defects. FIG. 9 is just for exemplifying this kind of modification by sp³ hybridization but does not show a repeating unit.

As known to the skilled person, Stone-Wales (SW) defects are topological defects in sp²-bonded carbon materials such as graphene. SW defects involve an in-plane 90° rotation of two carbon atoms with respect to the midpoint of the bond, accompanied by the shift of two C—C bonds. Typically, in this transformation four hexagons are changed into two heptagons and two pentagons. Inverse Stone-Wales (ISW) defects are a result of the addition of two carbon atoms (ad-dimer effect) into the hexagonal sp² hybridized carbon network. Typically as a result of this transformation three hexagons are transformed into two pentagons and two heptagons.

In a preferred embodiment, the modification is a heteroatomic substitution.

Preferably, the heteroatom or heteroatomic group of the one or more heteroatomic substitution modifications of the repeating unit RU1 is selected from nitrogen, boron, phosphor and its oxides, silicon, oxygen, sulphur and its oxides, hydrogen, or any combination thereof.

Preferably, at least one of the carbon atom sites in the hexagonal sp² hybridized carbon network of the repeating unit RU1 is replaced by a modification, more preferably at least one of the carbon atoms in the hexagonal sp² hybridized carbon network of the repeating unit RU1 is replaced by the heteroatom or heteroatomic group. Preferably more than one of the carbon atoms in the hexagonal sp² hybridized carbon network of the repeating unit RU1 is replaced by the one or more modifications, more preferably by the one or more heteroatoms or heteroatomic groups. Preferably not more than 50% of the carbon atoms in the hexagonal sp² hybridized carbon network of a repeating unit are replaced by the modifications.

The repeating unit RU1 may comprise just one modification (e.g. a heteroatomic substitution modification). Alternatively, the repeating unit may contain two or more modifications. If the repeating unit comprises two or more modifications, these can be of the same type (e.g. exclusively heteroatomic substitution modifications) or include different types of modifications (e.g. at least one heteroatomic substitution modification in combination with at least one vacancy modification).

The number of modifications within the graphene nanoribbon repeating unit RU1 can vary over a broad range, depending on the desired final properties of the GNR.

On the other hand, as already indicated above, it can be preferred that the number of modifications of the repeating unit is not too high. Preferably, the ratio of the number of modified carbon sites to the number of unmodified carbon atoms of the hexagonal sp² hybridized carbon network in the repeating unit R1 does not exceed 0.5.

If the repeating unit RU1 comprises heteroatomic substitution modifications, the ratio of the number of heteroatoms in the hexagonal sp² hybridized carbon network of said repeating unit to the number of carbon atoms in the hexagonal sp² hybridized carbon network of said repeating unit is 0.5 or less.

The location of the at least one modification in the repeating unit RU1 can be varied, depending on the desired properties of the final GNR. The one or more modifications can be located on the edge of and/or peripheral and/or central in the hexagonal sp² hybridized carbon network of the repeating unit RU1.

As will be discussed below in further detail, the graphene nanoribbon containing controlled modifications is preferably obtained by polymerizing at least one substituted or unsubstituted polycyclic aromatic monomer compound and/or at least one substituted or unsubstituted oligo phenylene aromatic monomer compound, followed by partial or complete cyclodehydrogenation of the polymer. Substituted or unsubstituted polycyclic aromatic monomer compounds from which the repeating unit of the grapheme nanoribbon can be derived include e.g. naphthalene, anthracene, tetracene, pentacene, hexacene, heptacene, octacene, nonacene, phenanthrene, bisanthene, trisanthene, chrysene, pyrene, triphenylene, benzo[a]pyrene, perylene, coronene, all of which can be substituted or unsubstituted or one of their aromatic carbon atoms can be substituted by a heteroatom. Substituted or unsubstituted oligo phenylene aromatic monomer compounds from which the repeating unit of the graphene nanoribbon can be derived include e.g. biphenyl, triphenyl, tetraphenyl, pentaphenyl, hexaphenyl, heptaphenyl, octaphenyl, all of which can be substituted or unsubstituted or one of their aromatic carbon atoms can be substituted by a heteroatom.

Preferably, the repeating unit RU1 of the graphene nanoribbon is derived from at least one aromatic monomer compound which is selected from at least one substituted or unsubstituted polycyclic aromatic monomer compound, at least one substituted or unsubstituted oligo phenylene aromatic monomer compound, or combinations thereof.

In a preferred embodiment, the aromatic monomer compound comprises at least one heterocyclic ring, which can be aromatic or non-aromatic. The one or more heteroatoms of said heterocyclic ring are preferably selected from those heteroatoms already mentioned above. The one or more heteroatoms of said heterocyclic ring preferably generate the heteroatomic substitution modification.

In a preferred embodiment, the polycyclic aromatic monomer compound comprises two or more annelated aromatic rings and at least one of the annelated aromatic rings comprises one or more heteroatoms (such as nitrogen, boron, phosphor and its oxides, oxygen, silicon, sulphur and its oxides, or any combination thereof).

For example, the aromatic monomer compound has one of the following formulas 2 to 4:

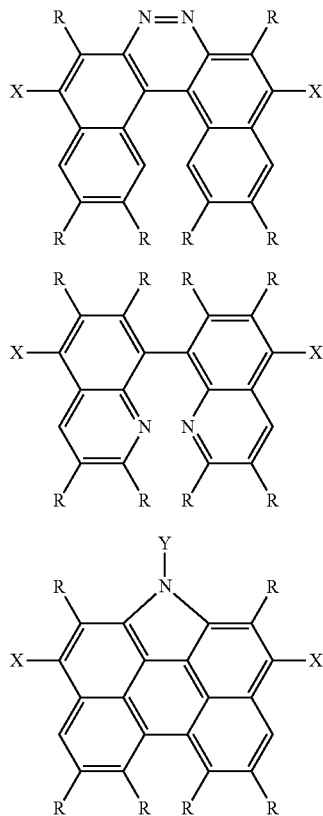

wherein
X, independently from each other, are a leaving group, preferably Br or I;

Y is alkyl, aryl, or hydrogen; and
R, independently of each other, are hydrogen; linear or branched or cyclic $C_1$-$C_{12}$alkyl which is unsubstituted or substituted by one or more OH, $C_1$-$C_4$alkoxy, phenyl, or by CN; $C_2$-$C_{12}$alkyl which is interrupted by one or more non-consecutive O; halogen; OH; $OR_3$; $SR_3$; CN; $NO_2$; $NR_1R_2$; $(CO)R_3$; $(CO)OR_3$; $O(CO)OR_3$; $O(CO)NR_1R_2$; $O(CO)R_3$; $C_1$-$C_{12}$alkoxy; $C_1$-$C_{12}$alkylthio; $(C_1$-$C_6$alkyl)-$NR_7R_8$; or —O—$(C_1$-$C_6$alkyl)$NR_1R_2$; aryl or heteroaryl (wherein aryl is preferably phenyl, biphenyl, naphthyl, or anthryl all of which are unsubstituted or are substituted by one or more $C_1$-$C_4$-alkyl, CN, $OR_3$, $SR_3$, $CH_2OR_3$, (CO) $OR_3$, $(CO)NR_1R_2$ or halogen); or two R together with the carbon atoms they are attached to form a 5-8-membered cycle or heterocycle;
$R_1$ and $R_2$ independently of each other are hydrogen, linear or branched $C_1$-$C_6$alkyl or phenyl, or $R_1$ and $R_2$ together with the nitrogen atom to which they are bonded form a group selected from

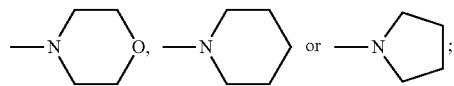

$R_3$ is H, $C_1$-$C_{12}$alkyl, phenyl which is unsubstituted or is substituted by one or more $C_1$-$C_4$alkyl, phenyl, halogen, $C_1$-$C_4$alkoxy or $C_1$-$C_4$alkylthio.

In a preferred embodiment, the repeating unit RU1 is derived from an aromatic monomer compound which is a polycyclic aromatic monomer compound comprising two or more annelated aromatic rings and at least one non-annelated heterocyclic residue being attached to at least one of the annelated aromatic rings. Alternatively, it can also be preferred that that the aromatic monomer compound is an oligo phenylene aromatic monomer compound which comprises at least one heterocyclic residue (either aromatic or non-aromatic) being attached to the phenylene group. As already mentioned above, the one or more heteroatoms or heteroatomic groups of the heterocyclic residue are preferably selected from nitrogen, boron, oxygen, sulphur and its oxides, phosphor and its oxides, or any combination thereof.

In a preferred embodiment, the aromatic monomer compound has the following formula 1:

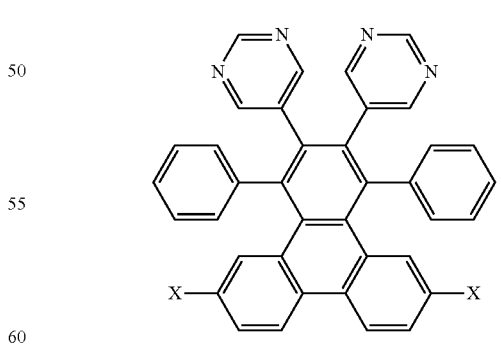

wherein
X, independently from each other, are a leaving group, preferably Br or I.

Figure 1:
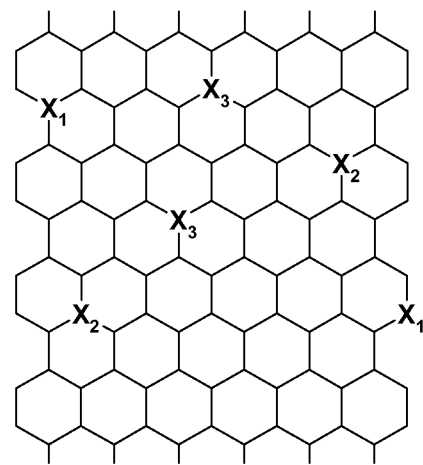
Figure 2:
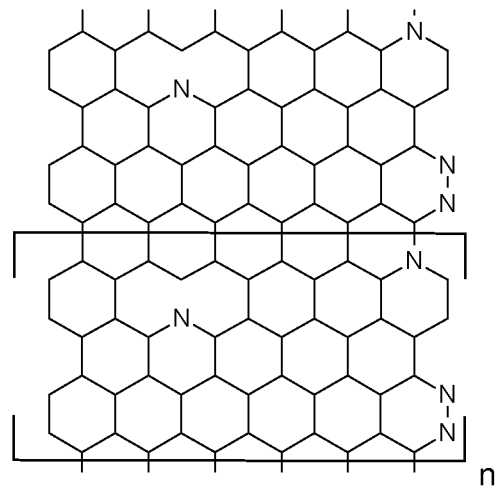
Figure 3:
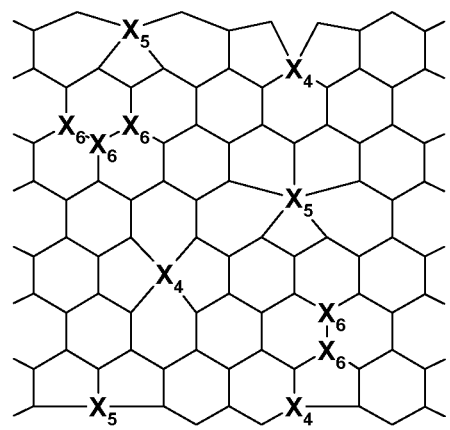
Figure 4:
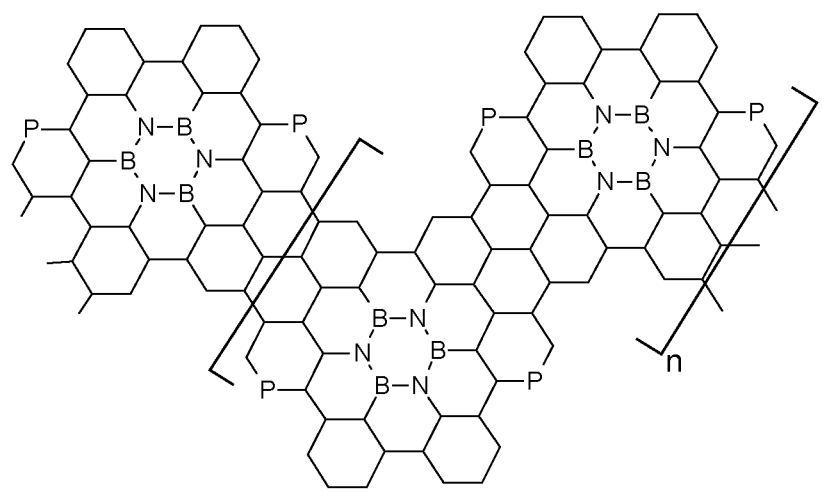
Figure 5:
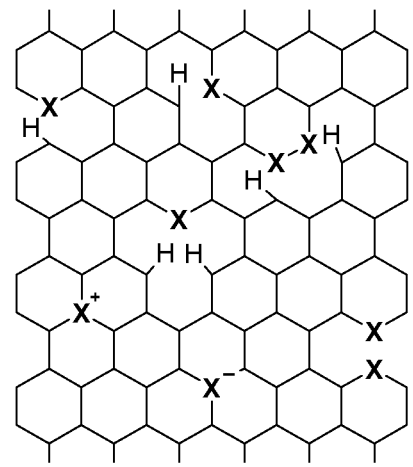
Figure 6:
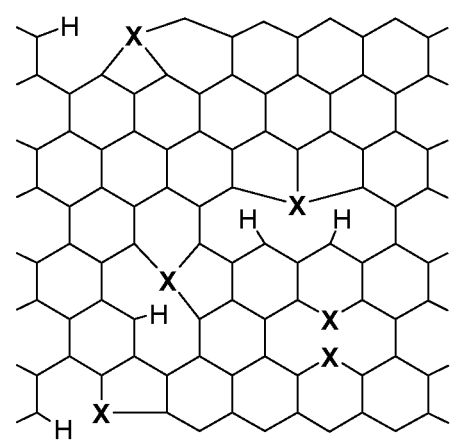
Figure 7:
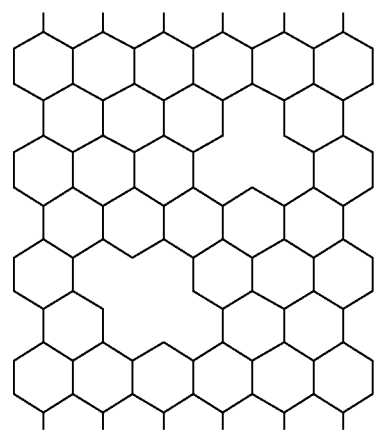
Figure 8:
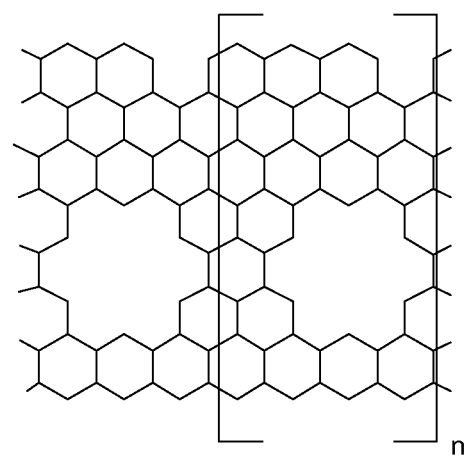
Figure 9:
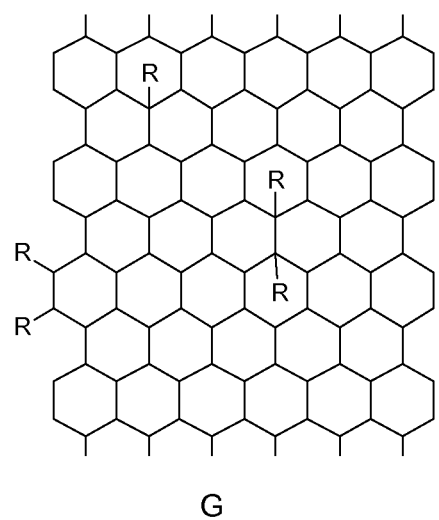
Figure 10:
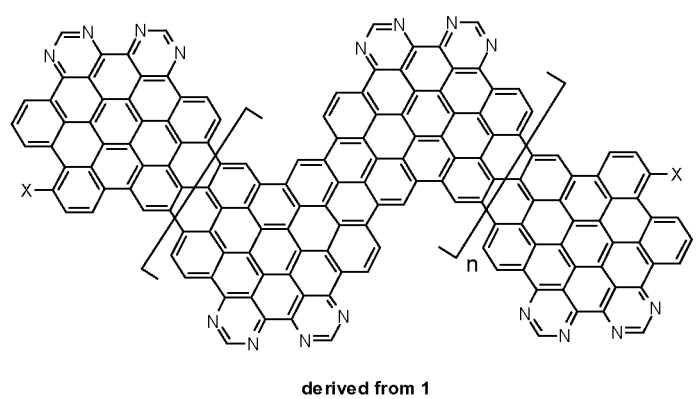
FIG. 10 shows a graphene nanoribbon comprising a repeating unit which is derived from the aromatic monomer compound of formula 1.
Figure 11:
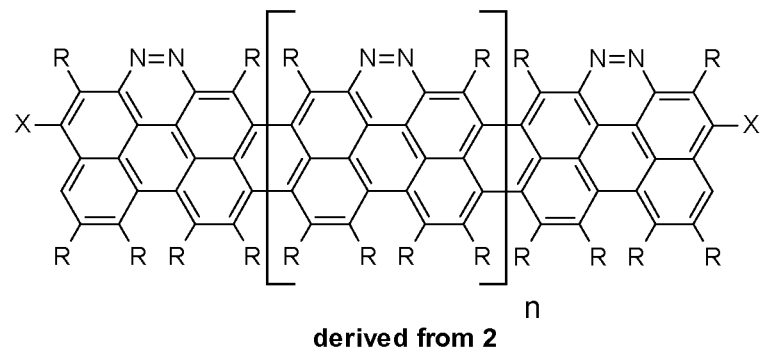
FIGS. 11 to 13 show graphene nanoribbons comprising monomer units derived from the aromatic monomer compounds of formulae 2 (FIG. 11), 3 (FIG. 12) and 4 (FIG. 13).
Figure 12:
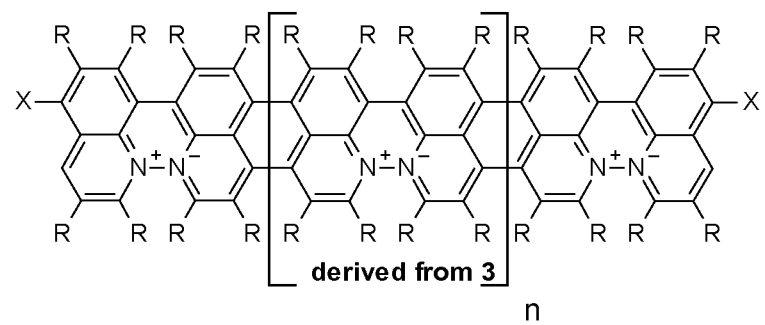
Figure 13:
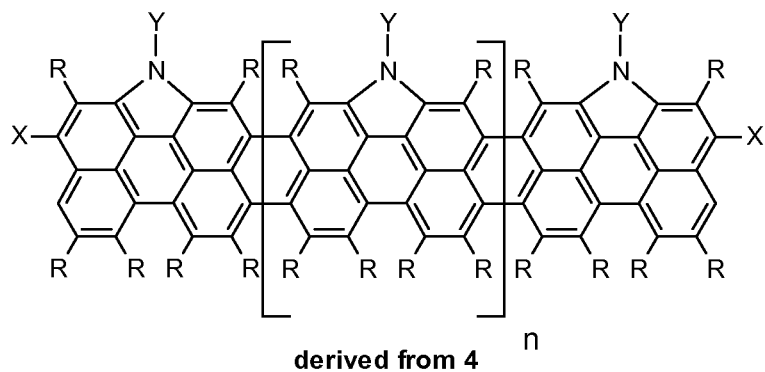

According to another preferred embodiment, the at least one substituted or unsubstituted polycyclic aromatic monomer compound and/or oligo phenylene aromatic monomer compound is of such a molecular structure that said monomer compound does not have a mirror plane perpendicular to the plane of the annelated aromatic rings or the aromatic phenylene group.

Due to this asymmetrical molecular structure, a repeating unit RU1 can be derived therefrom which includes one or more vacancy modifications.

However, in the present invention, it is also possible that a repeating unit RU1 including one or more vacancy modifications is derived from at least one symmetrical substituted or unsubstituted polycyclic aromatic monomer compound and/or oligo phenylene aromatic monomer compound.

The average width of the graphene nanoribbon can be varied over a broad range, depending on the desired final properties.

Preferably, the graphene nanoribbon or a segment of the graphene nanoribbon made of the repeating unit RU1 has a width of 20 nm or less, more preferably 10 nm or less, most preferably 4 nm or less.

The GNR width is measured with scanning tunneling microscopy (STM). The apparent width is corrected for the finite tip radius by STM simulation as explained in J. Cai et al., Nature 466, pp. 470-473 (2010). The STM images are simulated according to the Tersoff-Hamann approach with an additional rolling ball algorithm to include tip effects on the apparent ribbon width. The integrated density of states between the Fermi energy and the Fermi energy plus a given sample bias are extracted from a Gaussian and plane waves approach for the given geometries.

According to conventional notion, width of a graphene nanoribbon can also be expressed by the number N of dimer lines or carbon atom pairs across the width (K. Wakabayashi et al., Sci. Technol. Adv. Mater. 11 (2010) 054504). Just as an example, a fully annelated (i.e. fully cyclodehydrogenated) graphene nanoribbon derived from a pentacene monomer compound would have a number of dimer lines across the width of N=11.

Preferably, the repeating unit RU1 of the graphene nanoribbon can have a number N of dimer lines across the width of from 3 to 38, more preferably of from 3 to 21, or of from 5 to 20.

If the graphene nanoribbon comprises further repeating units RU2, RU3, . . . , the preferred width values indicated above apply to these additional repeating units as well.

According to another aspect, the present invention provides a process for preparing the graphene nanoribbon as disclosed above, which comprises:
(a) providing at least one polycyclic aromatic monomer compound and/or oligo phenylene aromatic monomer compound on a solid substrate,
(b) polymerization of the polycyclic aromatic and/or oligo phenylene aromatic monomer compound so as to form at least one polymer, which is preferably linear, on the surface of the solid substrate,
(c) at least partially cyclodehydrogenating the one or more polymers of step (b).

The polycyclic aromatic monomer compound and/or the oligo phenylene aromatic monomer compound of step (a) can be any compound which undergoes polymerization to a polymer (preferably a linear polymer) under appropriate reaction conditions. Such polycyclic aromatic monomer or oligo phenylene aromatic monomer compounds that can be reacted to a polymer are generally known to the skilled person.

Preferably, the polycyclic aromatic monomer and/or oligo phenylene aromatic monomer compound is substituted with at least two leaving groups, more preferably has at least two halogen substituents, preferably Br and/or I, which provide reactive sites for a subsequent polymerization reaction.

With regard to preferred polycyclic aromatic monomer and/or oligo phenylene aromatic monomer compounds, reference can be made to those aromatic monomer compounds already discussed above.

The type of monomer as exemplified by formula 1 can be prepared using a synthetic strategy as described e.g. in U.S. Pat. No. 7,968,872. The polycyclic aromatic monomer compound can for instance also be a Benzo[f]naphtho[2,1-c]cinnoline based compound such as a compound of formula 2 shown above and described by P. F. Holt and A. E. Smith in J. Chem. Soc., 1964, 6095, or a 8,8'-Biquinoline based compound such as a compound of formula 3 shown above and described in Tetrahedron Letters 53 (2012) 285-288, or a 1H-Phenanthro[1,10,9,8-cdefg]carbazole based compound such as a compound of formula 4 shown above and described in WO 2011/018144. A variety of such compounds is commercially available or can be prepared according to literature procedures by those skilled in the art. Reference can also be made to those polycyclic aromatic monomer compounds already mentioned above when discussing compounds from which the graphene segment repeating units are derived.

As indicated above, step (a) includes providing the at least one polycyclic aromatic monomer or oligo phenylene aromatic monomer compound on a solid substrate.

Any solid substrate enabling the deposition of the polycyclic aromatic monomer or oligo phenylene aromatic monomer compound and subsequent polymerization to a linear polymer on its surface can be used. Preferably, the solid substrate has a flat surface.

The flat surface on which the monomer compound is deposited can be a metal surface such as a Au, Ag, Cu, Al, W, Ni, Pt, or a Pd surface (which may be reconstructed or vicinal). The surface can be completely flat or patterned or stepped. Such patterned or stepped surfaces and manufacturing methods thereof are known to the skilled person. On patterned surfaces the growth of graphene nanoribbons may be directed by the surface pattern.

The surface may also be a metal oxide surface such as silicon oxide, silicon oxynitride, hafnium silicate, nitrided hafnium silicates (HfSiON), zirconium silicate, hafnium dioxide and zirconium dioxide, or aluminium oxide, copper oxide, iron oxide.

The surface may also be made of a semiconducting material such as silicon, germanium, gallium arsenide, silicon carbide, and molybdenum disulfide.

The surface may also be a material such as boron nitride, sodium chloride, or calcite.

The surface may be electrically conducting, semiconducting, or insulating.

The deposition on the surface may be done by any process suitable for providing organic compounds on a surface. The process may e.g. be a vacuum deposition (sublimation) process, a solution based process such as spin coating, spray coating, dip coating, printing, electrospray deposition, or a laser induced desorption or transfer process. The deposition process may also be a direct surface to surface transfer.

Preferably the deposition is done by a vacuum deposition process. Preferably it is a vacuum sublimation process. The vacuum may be in the range of $10^{-1}$ to $10^{-11}$ mbar.

As indicated above, step (b) of the process of the present invention includes polymerization of the polycyclic aromatic monomer and/or oligo phenylene aromatic monomer compound so as to form at least one polymer, which is preferably linear, on the surface of the solid substrate.

Appropriate conditions for effecting polymerization of the polycyclic aromatic monomer and/or oligo phenylene aromatic monomer compound are generally known to the skilled person.

Preferably, the polymerization in step (b) is induced by thermal activation. However, any other energy input which induces polymerization of the polycyclic aromatic monomer and/or oligo phenylene aromatic monomer compound such as radiation can be used as well.

The activation temperature is dependent on the employed surface and the monomer and can be in the range of from 0 to 500° C.

Optionally, step (a) and/or step (b) can be repeated at least once before carrying out partial or complete cyclodehydrogenation in step (c). When repeating steps (a) and (b), the same monomer compound or a different polycyclic aromatic monomer and/or oligo phenylene aromatic monomer compound can be used.

As indicated above, step (c) of the process of the present invention includes at least partially cyclodehydrogenating the one or more polymers of step (b).

In general, appropriate reaction conditions for cyclodehydrogenation are known to the skilled person.

In a preferred embodiment, the polymer of step (b) is subjected to complete cyclodehydrogenation.

In one embodiment, at least two different polycyclic aromatic monomer or oligo phenylene aromatic monomer compounds are provided on the solid substrate in step (a).

According to this embodiment, two or more different monomer compounds, preferably having similar reactivity, are provided in the liquid medium or on the surface of the solid substrate, followed by inducing polymerization to form a co-polymer, preferably a linear co-polymer. Subsequently, a partial or complete cyclodehydrogenation reaction is carried out leading to a segmented graphene nanoribbon.

In a variation of this embodiment, a first polycyclic aromatic monomer or oligo phenylene aromatic monomer compound is deposited on the surface of the solid substrate, followed by inducing polymerization to form a polymer, preferably a linear polymer. A second monomer is then deposited on the same substrate surface, followed by inducing polymerization to form a block co-polymer, preferably a linear block co-polymer. This step may optionally be repeated several times, either with identical or different monomer compounds to yield a multi block copolymer. Subsequently, the block co-polymer is subjected to a partial or complete cyclodehydrogenation reaction leading to a segmented graphene nanoribbon.

In another embodiment, the partial or complete cyclodehydrogenation reaction is induced by a spatially controlled external stimulus.

The external stimulus may be an electrical current, heat, an ion beam, oxidative plasma, microwave, light or electromagnetic radiation in general or it may be an oxidative chemical reagent. The spatial control of the activation may be done using a highly focused activation stimulus whose position versus the substrate can be controlled. The spatially confined activation stimulus may originate from a nano sized electrode, such as e.g. a tip of a tunneling microscope or from highly focused electromagnetic radiation such as e.g. a focused laser beam, or from a highly focused electron beam such as in an electron microscope. The spatial control of the activation may also be done using a nanostructured mask to direct the impact of the activation stimulus, such as e.g. a photomask.

The resulting graphene nanoribbons may be used directly on the substrate on which they are prepared or they may be transferred to another substrate.

The graphene nanoribbon (GNR) wherein the position of modifications and the distance between modifications as well as the number of modifications per repeating unit RU1 is precisely controlled may also be prepared via a solution based process, as already mentioned above and generally known to those skilled in the art. The process preferably comprises a solution polymerization of the at least one polycyclic aromatic monomer compound and/or oligo phenylene aromatic monomer compound to an oligo-phenylene precursor polymer (which is preferably linear) which can then be transformed into a controlled modification containing graphene nanoribbon using a solution based process such as cyclodehydrogenation (e.g. Scholl-type oxidative cyclodehydrogenation).

According to a further aspect, the present invention provides a compound of formula 1:

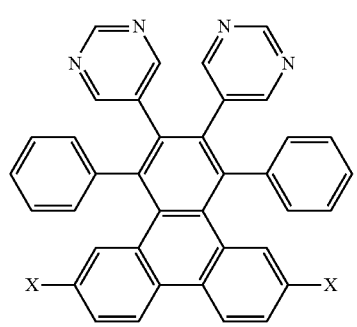

wherein

X, independently from each other, are a leaving group, preferably Br or I.

According to a further aspect, the present invention relates to the use of the aromatic monomer compounds as described above for preparing a graphene nanoribbon having a defined modification structure.

"Defined modification structure" means that the position of modifications and the distance between modifications as well as the number of modifications per repeating unit is precisely controlled. If the modification is for example a heteroatomic substitution modification, a substitutionally heteroatom functionalized graphene nanoribbon (GNR) is provided wherein the position of heteroatom substituents and the distance between substituents as well as the number of heteroatom substituents is precisely controlled.

EXAMPLES

1. Experimental Details 5,10-Dibromo-1,3-diphenyl-2Hcyclopenta[l]phenanthrene-2-on is prepared according to WO2008/012250, Example 1a.

The monomer 5,5'-(6,11-Dibromo-1,4-diphenyltriphenylen-2,3-diyl)dipyrimidine (1) is prepared as follows:

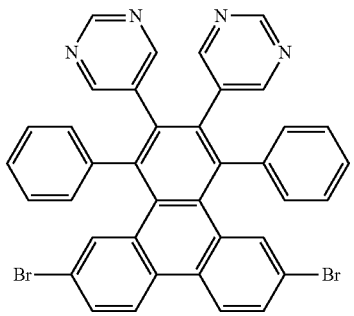

A dry and inert 25 ml Schlenk tube which is equipped with a magnetic stirrer and contained 5,10-dibromo-1,3-diphenyl-2H-cyclopenta[l]phenanthrene-2-on (0.711 g, 1.316 mmol) and dipyrimidyl tolan (0.200 g, 1.097 mmol) was repeatedly evacuated and purged with argon. Then, diphenyl ether (6 ml) was added. A freezing-thawing cycle was carried out and repeated twice so as to remove water and residual oxygen. Subsequently, the medium was stirred at 220° C. for 14 hours under a moderate argon flow. The light green solution turned into a brown suspension. After cooling the reaction medium to room temperature, a precipitation step was carried out in hexane: dichloromethane (hexane: dichloromethane, 200:2, v:v). The glaucous residue was separated via flash column chromatography (silica, ethyl acetate:hexane, 3:1 v:v) and compound 1 was obtained as an orange powder in an amount of 73 mg (0.105 mmol, 8%).

$^1$H-NMR: (300 MHz, $CD_2Cl_2$)=8.81 (s, 2H); 8.31 (s, 1H); 8.28 (s, 1H), 8.10 (s, 4H); 7.74 (d, 2H); 7.59 (d, 1H); 7.57 (d, 1H); 7.3-7.2 (m, 6H); 7.1-7.0 (m, 4H) ppm.

Melting point: 349.1° C. (ethyl acetate/hexane), discolouration

Preparation of GNRs.

Au(111) single crystals (Surface Preparation Laboratory, Netherlands) as well as 200 nm Au(111) thin films epitaxially grown on mica (Phasis, Switzerland) were used as substrates for GNR growth. Substrate surfaces were cleaned by repeated cycles of argon ion bombardment and annealing to 470° C. Precursor monomers were deposited onto the clean substrate surfaces by sublimation from a 6-fold evaporator (Knudsen-cell-type) at rates of ~2 Å/min. For the fabrication of the nitrogen substituted N=6/N=9 chevron-type armchair GNRs, the substrate was maintained at 200° C. during monomer deposition to induce dehalogenation and radical addition. After deposition, the sample was post-annealed at 400° C. for 10 min to cyclohydrogenate the polymers and form GNRs. All these steps were performed under ultra-high vacuum conditions.

STM Characterization of GNRs.

A variable-temperature STM (VT-STM) from Omicron Nanotechnology GmbH, Germany, was used to characterize the morphology of the GNR samples. Images were taken in the constant current mode under ultra-high vacuum conditions at sample temperatures of 298 K (room temperature) or 35 K (LHe cooling).

XPS Characterization of GNRs.

An ESCA system from Oimcron Nanotechnology GmbH, Germany, working under ultra-high vacuum conditions was used to determine the chemical composition of the GNRs. X-ray photoelectron spectroscopy (XPS, hv=1486.7 eV) of the C1s and N1s core levels is used for a quantitative intensity analysis, as described by P. Ruffieux et al. (Rev. Sci. Instr. 2000, 71, 3634-3639). GNR samples are grown in the STM chamber as described above and transferred through ambient conditions to the ESCA system. Transfer related volatile contaminations are removed by annealing the sample directly in the ESCA system to 200° C. under ultra-high vacuum conditions. Overview spectra assure that no contributions other than from GNR and the clean Au substrate are present.

FIG. 14 shows the bottom-up fabrication of nitrogen substituted chevron-type GNRs, i.e. a graphene nanoribbon having a repeating unit which comprises heteroatomic substitution modifications. The repeating unit comprising heteroatomic substitution modifications is derived from the aromatic monomer compound 1.

Precursor 1 is for bottom-up fabrication of nitrogen substituted chevron-type GNRs with two steps: formation of linear polymers by covalent interlinking of the dehalogenated intermediates after annealing at 470K; formation of fully aromatic GNRs by cyclodehydrogenation at 670K.

FIGS. 15a to 15d show measurements of the nitrogen substituted chevron-type GRN prepared according to the process described above. FIG. 15a shows an overview STM image of chevron-type GNR in the polymer state after surface-assisted C—C coupling of monomer 1 (T=35 K, U=1.0 V, I=0.05 nA). The inset displays a line profile along the indicated (line in bottom left corner) path and reveals an apparent polymer height of 0.31 nm. FIG. 15 b shows a small-scale STM image of the polymer chains (T=35 K, U=−1.0 V, I=0.07 nA) with partly overlaid chemical model. FIG. 15 c shows an overview STM image after cyclodehydrogenation at 670K (T=35 K, U=1.0 V, I=0.1 nA). The inset displays the profile along the indicated line path in the bottom left corner in c and reveals a cyclodehydrogenation-related reduction of the apparent height to 0.20 nm. FIG. 15d shows a small-scale STM image with partly overlaid structural model of the ribbon (T=35 K, U=−1.3 V, I=0.3 nA).

FIGS. 16a to 16c show STM and XPS measurements of nitrogen substituted chevron-type GNR prepared according to the process described above. FIGS. 16d to 16f show reference measurements for chevron-type ribbons based on monomer 5. FIG. 16a shows an STM overview image of a monolayer sample of nitrogen substituted chevron GNRs on Au(111) based on monomer 1 (T=35 K, U=1.5 V, I=0.03 nA). FIGS. 16b and 16c show C1s and N1s core-level spectra, respectively, for a monolayer sample of nitrogen-substituted chevron GRNs on Au(111) sample. The intensity ratio of $I_{N1s}/I_{C1s}$ is 0.14±0.05, in agreement with the expected ratio of 0.20. FIG. 16d shows an STM image of a monolayer sample of unmodified chevron GNRs on Au(111) (T=300K, U=2.0 V, I=0.02 nA) based on precursor monomer 5 (inset). FIGS. 16e and 16f show C1s and N1s core-level spetra, respectively, of chevron-type GNRs based on 5 using exactly the same analysis parameters as for FIGS. 16b and 16c, respectively.

The invention claimed is:
1. A graphene nanoribbon, comprising:
a repeating unit RU1 which comprises at least one modification,
wherein the modification is selected from the group consisting of a heteroatomic substitution, a vacancy, a $sp^a$ hybridization, a Stone-Wales defect, an inverse Stone-Wales defect, a hexagonal $sp^2$ hybridized carbon network ring size modification, and any combination thereof.

2. The graphene nanoribbon according to claim 1, wherein the at least one heteroatomic substitution modification of the repeating unit RU1 comprises a heteroatom or a heteroatomic group selected from nitrogen, boron, phosphor and oxides thereof, silicon, oxygen, sulphur and oxides thereof, hydrogen, and any combination thereof.

3. The graphene nanoribbon according to claim 1, wherein the repeating unit RU1 is derived from at least one aromatic monomer compound which is selected from the group consisting of at least one substituted or unsubstituted polycyclic aromatic monomer compound, at least one substituted or unsubstituted oligo phenylene aromatic monomer compound, and any combination thereof.

4. The graphene nanoribbon according to claim 3, wherein the aromatic monomer compound comprises at least one aromatic or non-aromatic heterocyclic ring.

5. The graphene nanoribbon according to claim 3, wherein the polycyclic aromatic monomer compound comprises two or more annelated aromatic rings and at least one of the annelated aromatic rings comprises one or more heteroatoms.

6. The graphene nanoribbon according to claim 3, wherein the polycyclic aromatic monomer compound comprises two or more annelated aromatic rings and at least one non-annelated heterocyclic residue is attached to at least one of the annelated aromatic rings; and/or the oligo phenylene aromatic monomer compound comprises at least one heterocyclic residue being attached to the phenylene group.

7. The graphene nanoribbon according to claim 3, wherein the aromatic monomer compound has one of the following formulas 2 to 4:

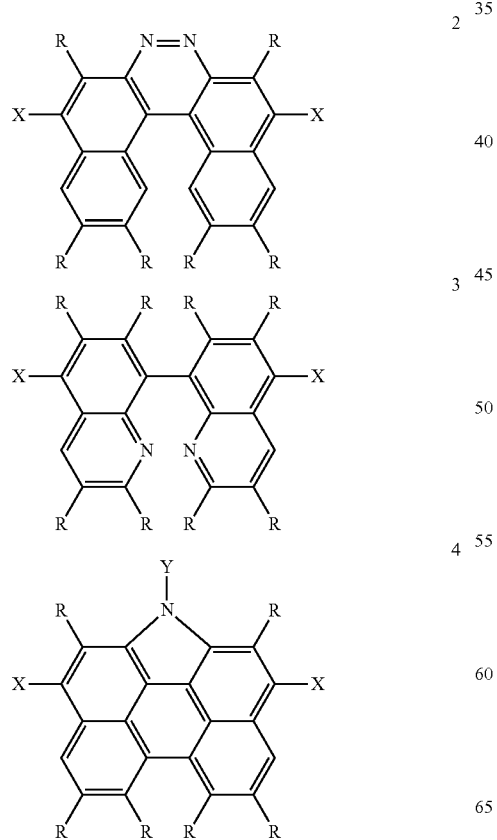

wherein:

X is each independently a leaving group;

Y is alkyl, aryl, or hydrogen; and

R is each independently selected from the group consisting of hydrogen; linear or branched or cyclic $C_1$-$C_{12}$ alkyl which is unsubstituted or substituted by one or more OH, $C_1$-$C_4$ alkoxy, phenyl, or CN; $C_2$-$C_{12}$ alkyl which is interrupted by one or more non-consecutive O; halogen; OH; $OR_3$; $SR_3$; CN; $NO_2$; $NR_1R_2$; $(CO)R_3$; $(CO)OR_3$; $O(CO)OR_3$; $O(CO)NR_1R_2$; $O(CO)R_3$; $C_1$-$C_{12}$ alkoxy; $C_1$-$C_{12}$ alkylthio; $(C_1$-$C_6$alkyl)-$NR_7R_8$; —O—$(C_1$-$C_6$alkyl)$NR_1R_2$; aryl or heteroaryl which is unsubstituted or substituted by one or more $C_1$-$C_4$-alkyl, CN, $OR_3$, $SR_3$, $CH_2OR_3$, $(CO)OR_3$, $(CO)NR_1R_2$ or halogen); or two R's together with the carbon atoms they are attached to form a 5-8-membered cycle or heterocycle;

wherein:

$R_1$ and $R_2$ independently of each other are hydrogen, linear or branched $C_1$-$C_6$ alkyl or phenyl, or $R_1$ and $R_2$ together with the nitrogen atom to which they are bonded form a group selected from the group consisting of

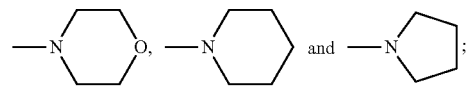

$R_3$ is selected from the group consisting of H, $C_1$-$C_{12}$ alkyl, phenyl which is unsubstituted or is substituted by one or more $C_1$-$C_4$ alkyl, phenyl, halogen, $C_1$-$C_4$ alkoxy and $C_1$-$C_4$alkylthio.

8. The graphene nanoribbon according to claim 3, wherein the aromatic monomer compound has the following formula 1:

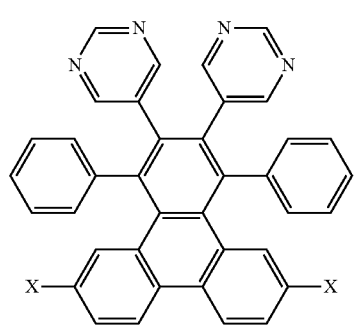

wherein

X is each independently a leaving group.

9. The graphene nanoribbon according to claim 7, wherein the graphene nanoribbon comprises one of the following structures:

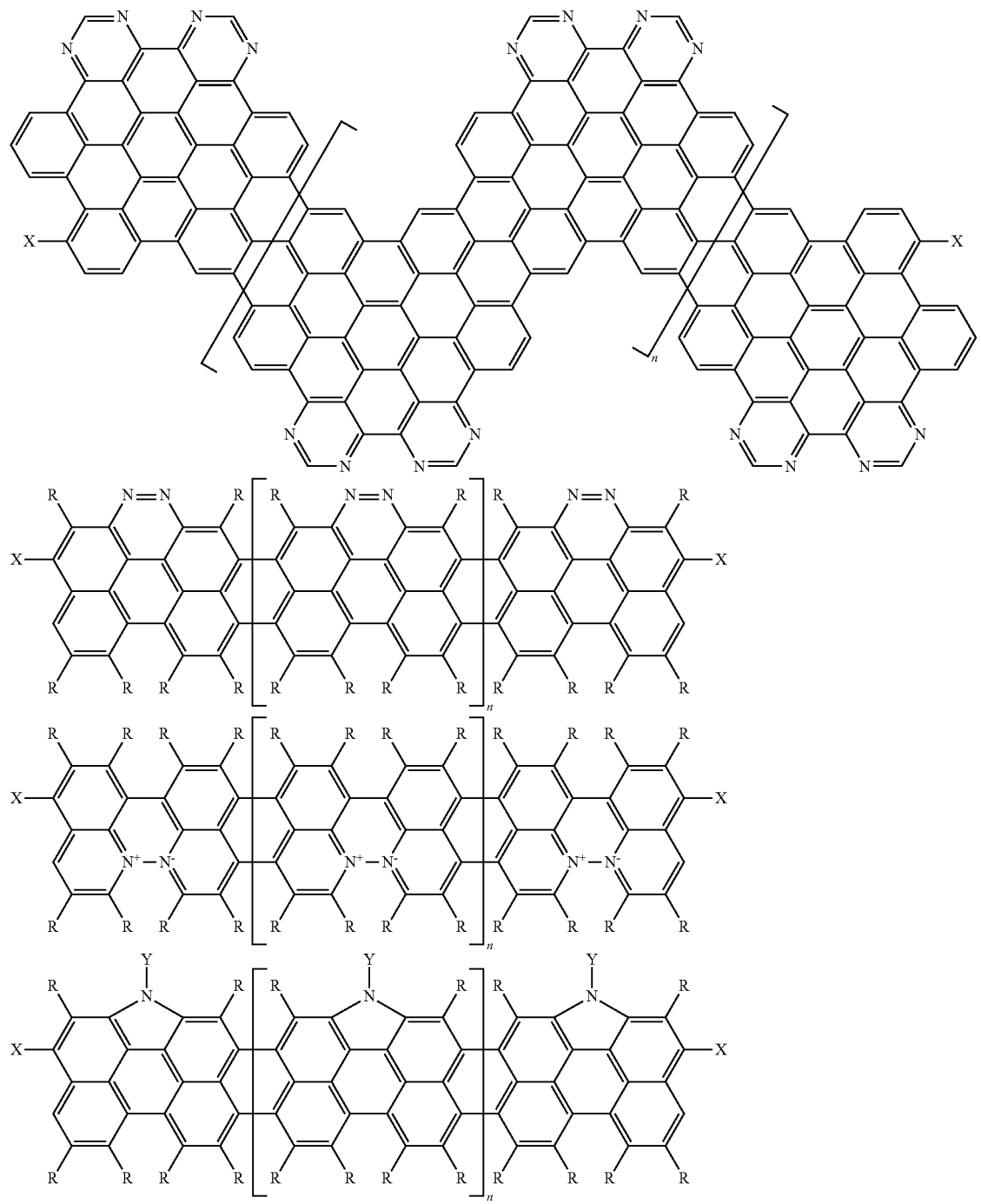

wherein:

X, Y, and R are as defined in claim 7, and n≤2500.

10. A process for preparing the graphene nanoribbon according to claim 1, which comprises:

(a) providing at least one aromatic monomer compound which is selected from the group consisting of at least one substituted or unsubstituted polycyclic aromatic monomer compound, at least one substituted or unsubstituted oligo phenylene aromatic monomer compound, and combinations thereof, on a solid substrate, (b) polymerizing the aromatic monomer compound and forming at least one polymer on the surface of the solid substrate, and (c) at least partially cyclodehydrogenating the at least one polymer of (b).

11. The process according to claim 10, wherein the polymerizing in (b) is induced by thermal activation.

12. The process according to claim 10, wherein the aromatic monomer compound is a polycyclic aromatic monomer compound and/or an oligo phenylene aromatic monomer compound.

* * * * *